United States Patent
Bae

(10) Patent No.: US 6,836,322 B2
(45) Date of Patent: Dec. 28, 2004

(54) PARTICLE INSPECTION DEVICE AND INSPECTION METHOD USING THE SAME

(75) Inventor: Sang-man Bae, Cheongju-shi (KR)

(73) Assignee: Hynix Semiconductor Inc., Gyunggi-do (JP)

( * ) Notice: Subject to any disclaimer, the term of this patent is extended or adjusted under 35 U.S.C. 154(b) by 0 days.

(21) Appl. No.: 10/331,386

(22) Filed: Dec. 30, 2002

(65) Prior Publication Data

US 2004/0012776 A1 Jan. 22, 2004

(30) Foreign Application Priority Data

Jul. 16, 2002 (KR) .................................. 10-2002-0041799

(51) Int. Cl.[7] .............................................. G01N 21/00
(52) U.S. Cl. ................................ 356/237.4; 356/237.1; 356/244; 250/372
(58) Field of Search ........................... 356/237.1–237.6, 356/244; 430/5, 394; 250/372, 360.1, 559.16, 559.18, 559.1

(56) References Cited

U.S. PATENT DOCUMENTS

| | | | |
|---|---|---|---|
| 4,529,299 A | * | 7/1985 | Banks et al. ................ 355/55 |
| 4,669,885 A | | 6/1987 | Ina ............................ 356/443 |
| 5,337,140 A | * | 8/1994 | Hagiwara et al. ......... 356/237.3 |
| 5,563,702 A | | 10/1996 | Emery et al. ................ 356/73 |
| 5,625,193 A | * | 4/1997 | Broude et al. ............. 250/372 |
| 5,737,072 A | | 4/1998 | Emery et al. ................ 356/73 |
| 6,052,478 A | | 4/2000 | Wihl et al. .................. 382/144 |
| 6,194,101 B1 | * | 2/2001 | Yano ............................ 430/5 |
| 6,246,773 B1 | * | 6/2001 | Eastty ...................... 381/71.11 |
| 6,282,309 B1 | | 8/2001 | Emery ....................... 382/145 |
| 6,363,166 B1 | | 3/2002 | Wihl et al. .................. 382/144 |

FOREIGN PATENT DOCUMENTS

| | | | |
|---|---|---|---|
| JP | 55103727 A | * | 8/1980 |
| JP | 62076623 A | * | 4/1987 |

* cited by examiner

Primary Examiner—Gregory J. Toatley, Jr.
Assistant Examiner—Sang H. Nguyen
(74) Attorney, Agent, or Firm—Marshall, Gerstein and Borun LLP

(57) ABSTRACT

A multi-use holder of a particle inspection device and an inspection method using the same can inspect both a wafer and a photomask using a scattering type inspection device since the scattering of a laser light irradiated from a light source can be avoided by fabricating the multi-use holder in a wafer shape, providing a second mounting portion and a first mounting portion on the upper surface thereof and forming a coating portion on the upper surface of the multi-use holder thereon when disposing the multi-use holder on a chuck fixed to a supporter by a vacuum generator, thereby reducing costs and improving productivity.

10 Claims, 3 Drawing Sheets

US 6,836,322 B2

PARTICLE INSPECTION DEVICE AND INSPECTION METHOD USING THE SAME

BACKGROUND OF THE INVENTION

1. Field of the Invention

The present invention relates to a particle inspection device and an inspection method using the same, and more particularly, to a particle inspection device and an inspection method using the same which can inspect both a wafer and a photomask using a scattering type inspection device since the scattering of a laser light irradiated from a light source can be avoided by fabricating a multi-use holder in a wafer shape, providing a second mounting portion and a first mounting portion on the upper surface thereof and forming a coating portion on the upper surface of the multi-use holder thereon when disposing the multi-use holder on a chuck fixed to a supporter by a vacuum generator, thereby reducing costs and improving productivity.

2. Description of the Related Art

Defects generated in a semiconductor device during manufacturing must be inspected and removed before product is shipped so as to increase the quality and yield of the product. Currently, process induced defect inspection devices are classified into (1) wafer process inspection devices and (2) photo mask process inspection devices and LCD inspection devices.

Additionally, inspection devices adapted to an algorithm, which are mainly used for a wafer, include a defect inspection device using a pattern-to-pattern comparison method and a database inspection device commonly adapted to photomasks, LCD's, and the like. Besides, a die-to-die inspection device adapted to a wafer and a photomask is included. Typically, the database inspection takes much longer than the pattern-to-pattern inspection and the die-to-die inspection. In the database inspection of a photomask with a design rule of 0.15 $\mu$m level, it takes about two hours.

Generally, the photomask is a light transmitting quartz. Thus a technical method of inspecting defects on the photomask provides that the defects on the photomask are discriminated from normal chrome patterns or phase shift materials by analyzing information of reflectance light and transmittance light on the upper surface of the photomask.

On the contrary, since a method of inspecting defects on a wafer uses a non-transparent silicon substrate, it inspects defects only with reflectance light (reflectance method).

A method of inspecting a wafer mainly inspects defects using a laser light incident at an inclination. In some cases, the wafer is disposed on a chuck with a stage and is adsorbed and fixed by a vacuum. Then, a laser light is irradiated at an inclination from the side surface and then light scattered on a defective portion is detected. Next, whether a defect exits or not is determined by comparison with adjacent patterns (scattering method)

FIG. 1 is a schematic view showing the construction of a conventional particle inspection device. The construction of the particle inspection device for inspecting particles of a wafer will now be described. The particle inspection device includes: a wafer 5 with a chrome pattern 4 on an upper surface; a chuck 6 supporting the bottom of the wafer 5; a vacuum conduit 7 for supplying a vacuum pressure into the chuck 6 to adsorb and fix the wafer 5 thereon; a stage 8 supporting the bottom of the chuck 6 via a supporter; a light source 2 irradiating a laser light on the wafer 5 at an inclinational angle; and a CCD camera 1 receiving and analyzing the laser light irradiated from the light source 2 when it is reflected from a defective portion 3.

The operational state of the particle inspection device will be described. The wafer formed with a chrome pattern is mounted on the chuck 6 and is fixed by applying a vacuum pressure via the vacuum conduit 7.

In this state, a laser light is irradiated from the light source 2 and is reflected onto the defective portion 3. Then, the light incidents on the CCD camera 1 and detects a defect by analysis and by comparison with other patterns.

However, the above-described scattering method is only used for inspection of a non-light transmitting wafer. This scattering method is advantageous in that it takes much shorter time than the reflectance method.

In contrast, the reflectance method is mainly adapted to materials causing scattering with clear fields such as a photomask. But, it takes much more time for analysis, and this causes lower productivity.

SUMMARY OF THE INVENTION

It is, therefore, an object of the present invention to provide a particle inspection device and an inspection method using the same which can inspect both a wafer and a photomask using a scattering type inspection device since the scattering of laser light irradiated from a light source can be avoided by fabricating the multi-use holder in a wafer shape, providing a second mounting portion and a first mounting portion on the upper surface thereof and forming a coating portion on the upper surface of the multi-use holder thereon when disposing the multi-use holder on a chuck fixed to a supporter by a vacuum generator, thereby reducing the cost and improving productivity.

In accordance with an aspect of the present invention, there is provided a particle inspection device, comprising: a multi-use holder being provided with a first mounting portion and a second mounting portion on which the wafer and the photomask each having a chrome pattern on the upper surface are selectively mounted; a tray supporting the bottom surface of the multi-use holder; a chuck adsorbing and fixing the tray by vacuum; a supporter provided with a vacuum conduit and supporting the chuck; a vacuum generator supplying a vacuum pressure to the chuck via the vacuum conduit; a stage having the vacuum generator disposed thereon and horizontally moving the tray by means of the supporter; and a CCD camera receiving and analyzing a laser light irradiated from a light source disposed on the wafer at an inclination and reflected from a defective portion.

In accordance with another aspect of the present invention, there is provided a particle inspection device for inspecting particles of a wafer and a photomask, having: a chuck adsorbing and fixing an object mounted on the upper surface by vacuum; a supporter being provided with a vacuum conduit and supporting the chuck; a vacuum generator supplying a vacuum pressure to the chuck via the vacuum conduit; a stage having the vacuum generator disposed thereon and horizontally moving the tray by means of the supporter; and a CCD camera receiving and analyzing a laser light irradiated from a light source disposed on the wafer at an inclination and reflected from a defective portion, wherein the particle inspection device comprises a multi-use holder provided with a first mounting portion and a second mounting portion on which the wafer and the photomask each having a chrome pattern on the upper surface are selectively mounted and fixed by the chuck.

In accordance with yet another aspect of the present invention, there is provided an inspection method using a multi-use holder of a particle inspection device of a scattering type, comprising the steps of: mounting a photomask onto the multi-use holder provided with a first mounting portion for mounting a wafer and a second mounting portion for mounting a photomask; inserting a fixing material made of rubber into an insertion hole formed at a corner and forcedly fixing the same so as to prevent the photomask from being movable; mounting the multi-use holder having the photomask mounted thereon on a tray and adsorbing and fixing the same by applying vacuum to a chuck via a vacuum conduit from a vacuum generator; and analyzing a defect by a CCD camera after receiving the light scattered on a defective portion of the photomask, that is, the laser light irradiated from a light source.

In accordance with still another aspect of the present invention, there is provided an inspection method using a multi-use holder of a particle inspection device of a scattering type, comprising the steps of: mounting a wafer onto the multi-use holder provided with a first mounting portion for mounting a wafer and a second mounting portion for mounting a photomask; mounting the multi-use holder having the wafer mounted thereon on a tray and adsorbing and fixing the same by applying a vacuum to a chuck via a vacuum conduit from a vacuum generator; and analyzing a defect by a CCD camera after receiving the light scattered on a defective portion of the wafer, that is, the laser light irradiated from a light source.

BRIEF DESCRIPTION OF THE DRAWINGS

The above objects, features and advantages of the present invention will become more apparent from the following detailed description when taken in conjunction with the accompanying drawings, in which.

DETAILED DESCRIPTION OF THE PREFERRED EMBODIMENT

A preferred embodiment of the present invention will now be described with reference to the accompanying drawings.

Figure 1:
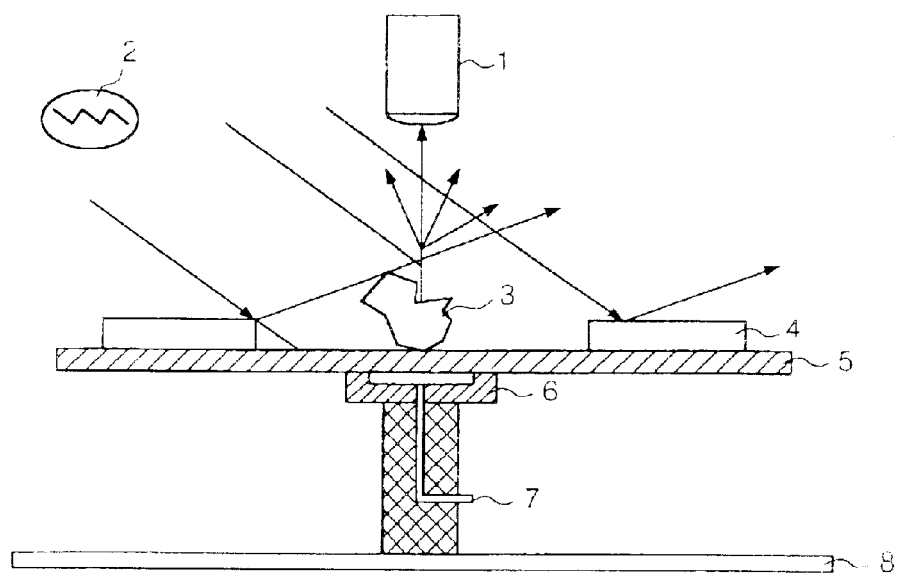
FIG. 1 is a schematic view showing the construction of a conventional particle inspection device.
Figure 2:
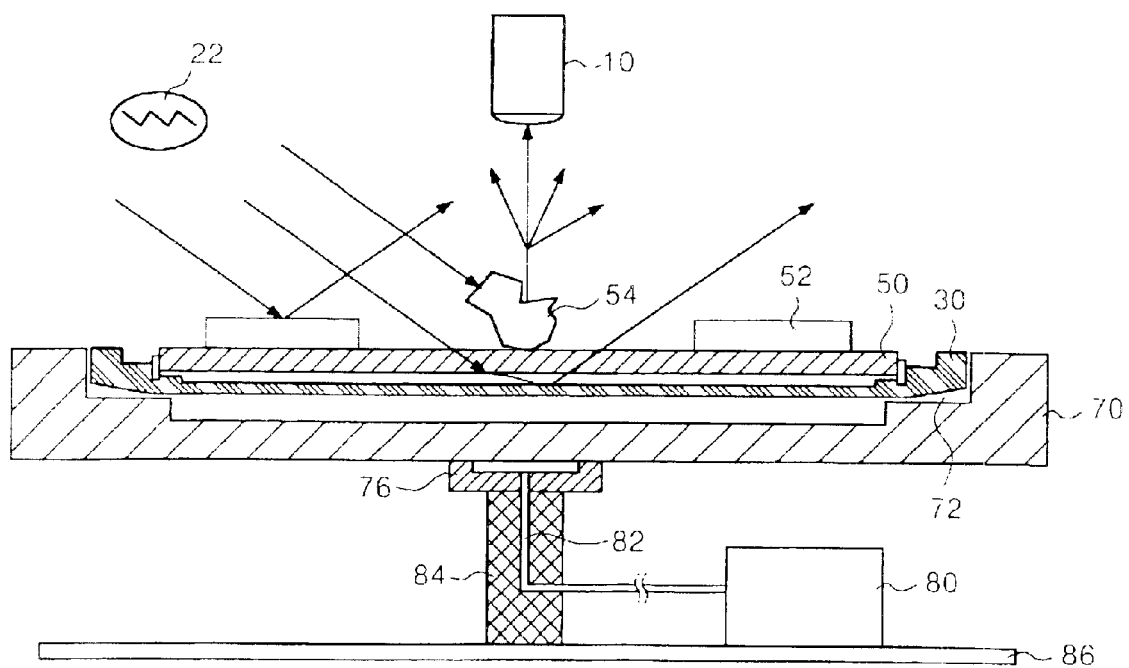
FIG. 2 is a schematic view showing a particle inspection device according to the present invention when a photomask is mounted and inspected.
Figure 3:
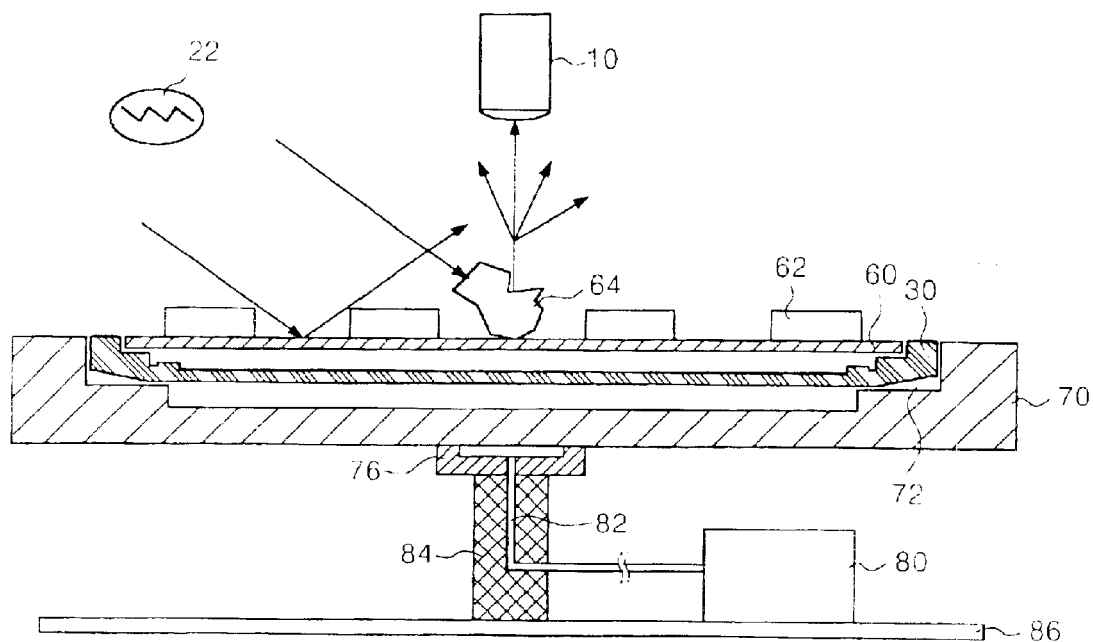
FIG. 3 is a schematic view showing the particle inspection device according to the present invention when a wafer is mounted and inspected.
Figure 4:
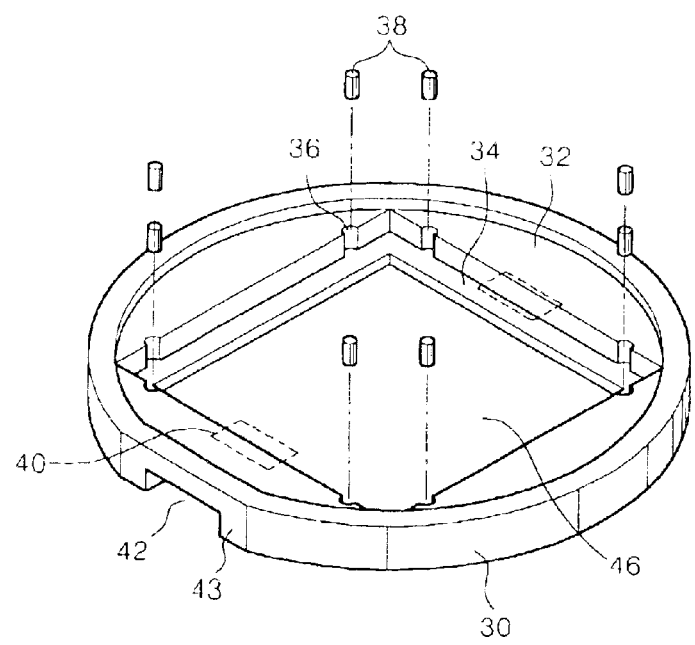
FIG. 4 is a perspective view of the multi-use holder according to the present invention.

FIG. 2 is a schematic view showing a particle inspection device according to the present invention when a photomask is mounted and inspected; FIG. 3 is a schematic view showing the particle inspection device according to the present invention when a wafer is mounted and inspected; and FIG. 4 is a perspective view of the multi-use holder according to the present invention;

According to the preferred embodiment of the present invention, the particle inspection device for inspecting particles of a wafer 60 and a photomask 50 includes: a multi-use holder 30 being provided with a first mounting portion 32 and a second mounting portion 34 on which the wafer 60 and the photomask 50 each having a chrome pattern 52 and 62 on the upper surface are selectively mounted; a tray 70 supporting the bottom surface of the multi-use holder 30; a chuck 76 adsorbing and fixing the tray 70 by a vacuum; a supporter 84 being provided with a vacuum conduit 82 and supporting the chuck 76; a vacuum generator 80 supplying vacuum pressure to the chuck 76 via the vacuum conduit 82; a stage 86 having the vacuum generator 80 disposed thereon and horizontally moving the tray 70 by means of the supporter 84; and a CCD camera 10 receiving and analyzing a laser light irradiated from a light source 22 disposed on the wafer 60 at an inclination angle and reflected from a defective portion 64.

Conventionally, a method of directly adsorbing and fixing the wafer 60 by vacuum using the chuck 76 was employed. However, in the present invention, a method of selectively adsorbing and fixing the multi-use holder 30 or the tray 70 by vacuum using the chuck 76 is employed in order to selectively inspect the wafer 60 and the photomask 50.

Figure 7:
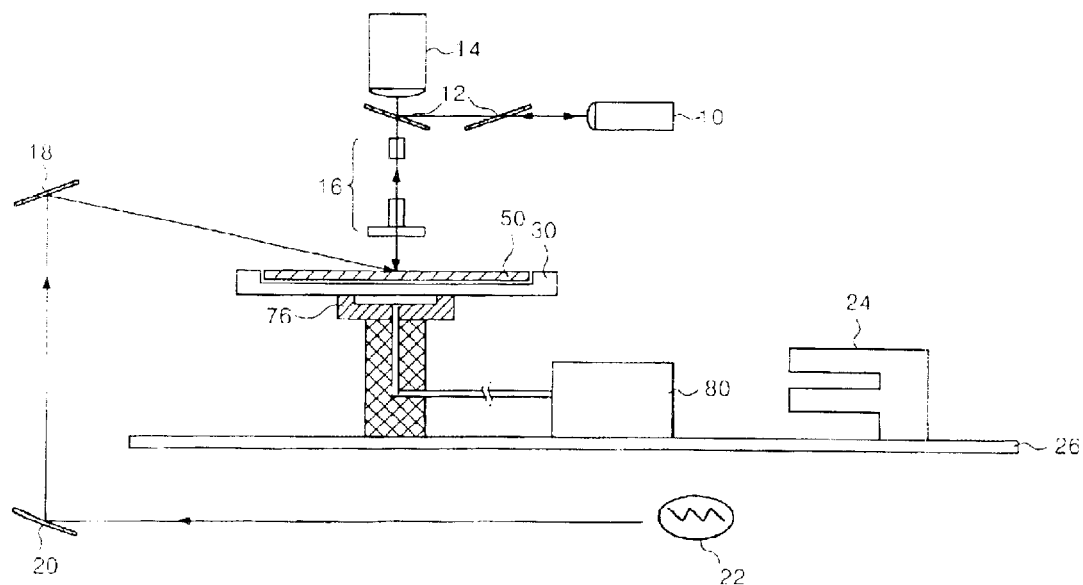
FIG. 7 is a schematic view showing the particle inspection device according to the present invention when it is used in a different way.

Therefore, when a vacuum pressure generated from the vacuum generator 80 is supplied to the chuck 76 via the vacuum conduit 82, the chuck 76 can adsorb and fix the tray 70 by vacuum as shown in FIGS. 2 and 3, or can directly adsorb and fix the multi-use holder 30 without disposing the tray 70 there between as shown in FIG. 7. Here, the tray 70 allows the multi-use holder 70 to be fixed to the chuck 76 in a more stable manner, thereby increasing the accuracy of the particle inspection.

Additionally, a conventional scattering-type inspection device can inspect only one wafer. However, the inspection device according to the preferred embodiment of the present invention employs the multi-use holder 30 capable of mounting a wafer 60 and a photomask 50 having different sizes and shapes.

For this, as shown in FIG. 4, the first mounting portion 32 and the second mounting portion 34 having different sizes are formed on the multi-use holder 30. Here, for example, the wafer 60 is mounted on the first mounting portion 32 as shown in FIG. 3, and the photomask 50 or a rectangular LCD substrate is mounted on the second mounting portion 34 as shown in FIG. 2.

Then, a black coating portion 44 is formed on the upper surface of the multi-use holder 30 in order to prevent the scattering of the laser light.

Then, the multi-use holder 30 is formed with an insertion hole 36 at a corner portion preventing the photomask 50 from being movable on the second mounting portion 34 and a soft fixing member 38 is inserted into the insertion hole 36 for fixing the photomask 50.

Preferably, the fixing member 38 is made of rubber and has a diameter of 3 to 4 mm.

On the bottom surface of the center portion of the multi-use holder 30 are formed a plurality of jig holes 40 for inserting a jig.

Preferably, the jig hole has a width of 3 mm and a length of 4 mm.

On a side surface of the multi-use holder 30 is formed a flat zone 43 for detecting a position by a sensor. On the bottom surface of the flat zone 43 is formed a holder loading recess 42 for loading the holder.

Preferably, the holder loading recess 42 has a width of 3 mm, a length of 4 mm and a depth of 3 to 4 mm.

Figure 5:
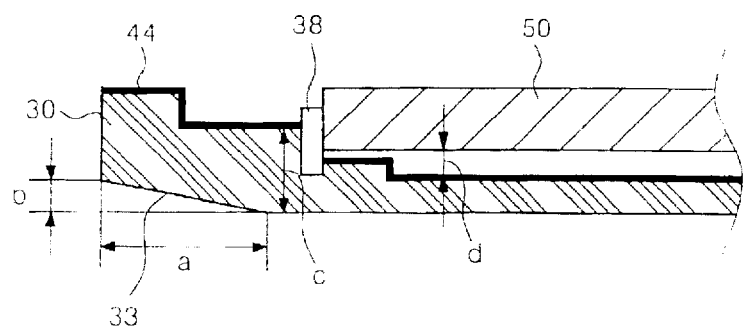
FIG. 5 is a cross-sectional view of the multi-use holder according to the present invention when the photomask is mounted.
Figure 6:
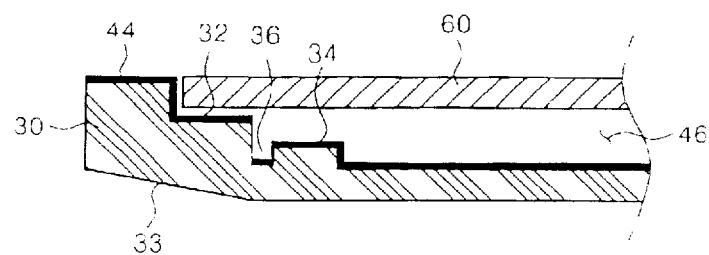
FIG. 6 is a cross-sectional view of the multi-use holder according to the present invention when the wafer is mounted.

FIG. 5 is a cross-sectional view of the multi-use holder according to the present invention when the photomask is mounted and FIG. 6 is a cross-sectional view of the multi-use holder according to the present invention when the wafer is mounted.

As shown therein, on the bottom of an edge of the multi-use holder 30 is formed a gradually inclining the surface portion 33, so that the multi-use holder 30 can be easily mounted on or demounted from a mounting portion 72 of the tray 70.

Preferably, the inclining surface portion 33 has a width (a) of 2 to 6 mm and a height (b) of 0.5 to 1.5 mm.

Preferably, the multi-use holder 30 has a thickness (c) of 5 to 7 mm between the second mounting portion 34 and the bottom surface.

And, the multi-use holder 30 has a thickness (d) of 0.3 to 1 mm between the second mounting portion 34 and the bottom surface of a space portion 46.

Preferably, the multi-use holder 30 is made of one of aluminum, glass fiber or hardened plastic.

The multi-use holder 30 can be used by applying a Teflon coating on an aluminum or other metallic material.

Hereinafter, an inspection method using a multi-use holder according to the present invention will now be described.

As shown in FIG. 2, a process of inspecting a photomask 50 using a scattering type inspection device will be described.

The photomask 50 is mounted on the multi-use holder 30 provided with a first mounting portion 32 for mounting a wafer 60 and a second mounting portion 34 for mounting the photomask 50.

After the above step, to prevent movement of the photomask 50, a fixing material 38 made of rubber is inserted into an insertion hole 36 which is formed at a corner and is forcedly fixed there into.

Next, the multi-use holder 30 having the photomask 50 mounted thereon is mounted on a tray 70. Then, the multi-use holder 30 is fixed by applying a vacuum to the chuck 76 via vacuum conduit 80 from the vacuum generator 80.

Thereafter, a CCD camera 10 analyzes a defect after receiving the light scattered on a defective portion 54 of the photomask 50, that is, the laser light irradiated from a light source 22.

The laser light irradiated from the light source 22 is incident on the CCD camera 10 by being reflected from a chrome pattern 52 formed on the photomask 50, being transmitted and reflected from the photomask 50 of quartz or being refracted and reflected from the defective portion 54 at a predetermined angle. The defect is analyzed by comparing this incident signal with the pattern and the defective portion.

At this time, a black coating portion 44 coated on the upper surface of the multi-use holder 30 can be a help to an inspection since it prevents the light irradiated from the light source 22 from being scattered unnecessarily.

Preferably, the incident angle of the light source 22 is 0.25 to 34 degrees. As shown in FIG. 3, a process of inspecting a wafer 60 using a scattering type inspection device will be described.

The wafer 60 is mounted on the multi-use holder 30 provided with a first mounting portion 32 for mounting the wafer 60 and a second mounting portion 34 for mounting a photomask 50.

Next, the multi-use holder 30 having the wafer 60 mounted thereon is mounted on a tray 70. Then, the multi-use holder 30 is adsorbed and fixed by applying vacuum to the chuck 76 via vacuum conduit 80 from the vacuum generator 80.

Thereafter, a CCD camera 10 analyzes a defect after receiving the light scattered on a defective portion 54 of the wafer 60, that is, the laser light irradiated from a light source 22.

Preferably, the incident angle of the light source 22 is 0.25 to 34 degrees.

The wafer 60 is made of a dark field flat material. Therefore, there is no difficulty in analysis since the laser light is not transmitted through the wafer 60 and thus is not scattered.

FIG. 7 is a schematic view showing the particle inspection device according to the present invention when it is used in a different way, in which the multi-use holder 30 of the present invention is directly adsorbed and fixed by using the chuck 76 without disposing the tray, 70 there between. The particle inspection device is used in such a manner that the multi-use holder 30 is adsorbed and fixed by the vacuum chuck 76 with the photomask 50 being disposed on the multi-use holder 30.

Then, the X-Y position of the multi-use holder 30 is aligned by moving a free alignment portion 24, with respect to stage 26.

In this state, a laser light is irradiated from the light source 22 on the photomask 50 at an angle via a mirror 20 and a rotating mirror 18.

The reflected light is analyzed, as it is incident on the CCD camera 10 and an image camera 14 via a lens portion 16 and a beam splitter 12.

As explained above, according to the multi-use holder of the particle inspection device and the inspection method using the same of the present invention, both a wafer and a photomask can be inspected using a scattering type inspection device since the scattering of a laser light irradiated from a light source can be avoided by fabricating the multi-use holder in a wafer shape, providing a second mounting portion and a first mounting portion on the upper surface thereof and forming a coating portion on the upper surface of the multi-use holder thereon when disposing the multi-use holder on a chuck fixed to a supporter by a vacuum generator, thereby reducing the costs and improving productivity.

Conventionally, it takes much time to inspect a photomask since only a reflectance method is used. However, the present invention is advantageous in that the inspection time is greatly reduced and workability is improved since the photomask is inspected using the scattering type inspection device.

What is claimed is:

1. A particle inspection device for inspecting particles on a wafer and a photomask, comprising:

a multi-use holder provided with a first mounting portion and a second mounting portion on which the wafer and the photomask each having a chrome pattern on the upper surface are selectively mounted, said multi-use holder defining an edge;

a tray supporting the bottom surface of the multi-use holder;

a gradually inclined surface portion formed on the bottom of the edge of the multi-use holder so that the multi-use holder can be easily mounted on or demounted from a mounting portion of the tray;

a chuck adsorbing and fixing the tray by vacuum;

a supporter provided with a vacuum conduit and supporting the chuck;

a vacuum generator supplying a vacuum pressure to the chuck via the vacuum conduit;

a stage having the vacuum generator disposed thereon and horizontally moving the tray by means of the supporter; and a CCD camera receiving and analyzing a laser light irradiated from a light source disposed on the wafer at an inclination angle and reflected from a defective portion.

2. The particle inspection device of claim 1, comprising a black coating portion formed on the upper surface of the multi-use holder in order to prevent the scattering of the laser light.

3. The particle inspection device of claim 1, wherein the multi-use holder comprises an insertion hole at a corner portion for preventing the photomask from being movable on a second mounting portion and a soft fixing member inserted into the insertion hole for fixing the photomask.

4. The particle inspection device of claim 1, comprising a plurality of jig holes formed on the bottom surface of the center portion of the multi-use holder.

5. The particle inspection device of claim 1, comprising a flat zone for detecting a position by a sensor formed on a side surface of the multi-use holder and a holder loading recess for loading the holder formed on the bottom surface of the flat zone.

6. The particle inspection device of claim 1, wherein the inclining surface portion has a width of 2 mm to 6 mm and a height of 0.5 m to 1.5 mm.

7. The particle inspection device of claim 1, wherein the multi-use holder has a thickness of 5 mm to 7 mm between the second mounting portion and the bottom surface.

8. The particle inspection device of claim 1, wherein the multi-use holder has a thickness of 0.3 mm to 1 mm between the second mounting portion and the bottom surface of a space portion.

9. The particle inspection device of claim 1, wherein the multi-use holder is made of aluminum, glass fiber or hardened plastic.

10. The particle inspection device of claim 1, wherein a rectangular LCD substrate is mounted on the second mounting portion of the multi-use holder.

* * * * *